(12) United States Patent
Nesterenko et al.

(10) Patent No.: US 10,512,903 B2
(45) Date of Patent: Dec. 24, 2019

(54) MODIFIED CRYSTALLINE ALUMINOSILICATE FOR DEHYDRATION OF ALCOHOLS

(71) Applicants: Total Research & Technology Feluy, Seneffe (Feluy) (BE); IFP Energies Nouvelles, Rueil Malmaison (FR)

(72) Inventors: Nikolai Nesterenko, Nivelles (BE); Delphine Minoux, Nivelles (BE); Nadiya Danilina, Leipzig (DE); Jean-Pierre Dath, Beloeil (BE); Vincent Coupard, Billeurbanne (FR); Sylvie Maury, Saint Maurice d'Argoire (FR)

(73) Assignees: TOTAL RESEARCH & TECHNOLOGY FELUY, Seneffe (BE); IFP ENERGIES NOUVELLES, Rueil Malmaison (FR)

(*) Notice: Subject to any disclaimer, the term of this patent is extended or adjusted under 35 U.S.C. 154(b) by 110 days.

(21) Appl. No.: 15/514,263

(22) PCT Filed: Sep. 24, 2015

(86) PCT No.: PCT/EP2015/071934
§ 371 (c)(1),
(2) Date: Mar. 24, 2017

(87) PCT Pub. No.: WO2016/046296
PCT Pub. Date: Mar. 31, 2016

(65) Prior Publication Data
US 2017/0304809 A1    Oct. 26, 2017

(30) Foreign Application Priority Data

Sep. 26, 2014   (EP) .................................. 14290289

(51) Int. Cl.
| | | |
|---|---|---|
| *B01J 29/06* | (2006.01) | |
| *B01J 29/67* | (2006.01) | |
| *B01J 29/65* | (2006.01) | |
| *B01J 29/66* | (2006.01) | |
| *B01J 29/68* | (2006.01) | |
| *B01J 29/69* | (2006.01) | |
| *B01J 37/02* | (2006.01) | |
| *B01J 29/70* | (2006.01) | |
| *B01J 29/90* | (2006.01) | |
| *C01B 39/02* | (2006.01) | |
| *C07C 1/24* | (2006.01) | |
| *C07C 5/27* | (2006.01) | |
| *B01J 37/30* | (2006.01) | |
| *C01B 39/44* | (2006.01) | |
| *B01J 29/74* | (2006.01) | |

(52) U.S. Cl.
CPC ............. *B01J 29/67* (2013.01); *B01J 29/061* (2013.01); *B01J 29/65* (2013.01); *B01J 29/655* (2013.01); *B01J 29/66* (2013.01); *B01J 29/68* (2013.01); *B01J 29/69* (2013.01); *B01J 29/70* (2013.01); *B01J 29/90* (2013.01); *B01J 37/0201* (2013.01); *B01J 37/30* (2013.01); *C01B 39/026* (2013.01); *C01B 39/44* (2013.01); *C07C 1/24* (2013.01); *C07C 5/2775* (2013.01); *B01J 29/74* (2013.01); *B01J 2229/10* (2013.01); *B01J 2229/16* (2013.01); *B01J 2229/186* (2013.01); *B01J 2229/34* (2013.01); *B01J 2229/37* (2013.01); *B01J 2229/42* (2013.01); *C07C 2529/65* (2013.01); *C07C 2529/66* (2013.01); *C07C 2529/67* (2013.01); *C07C 2529/68* (2013.01); *C07C 2529/69* (2013.01); *Y02P 20/584* (2015.11)

(58) Field of Classification Search
CPC . B01J 29/65; B01J 29/655; B01J 29/66; B01J 29/67; B01J 29/68; B01J 29/69; B01J 2229/10; B01J 2229/16; B01J 2229/186; B01J 2229/34; B01J 2229/37; B01J 37/30; B01J 37/0201; C07C 2529/65; C07C 2529/66; C07C 2529/67; C07C 2529/68; C07C 2529/69; C01B 39/44; C01B 39/026
USPC .......................................... 502/62, 73, 74, 85
See application file for complete search history.

(56) References Cited

U.S. PATENT DOCUMENTS

| | | |
|---|---|---|
| 4,282,389 A | 8/1981 | Droste et al. |
| 5,523,510 A | 6/1996 | Pellet et al. |

(Continued)

FOREIGN PATENT DOCUMENTS

| | | |
|---|---|---|
| EP | 2348005 A1 | 7/2011 |
| WO | 2011089235 A1 | 7/2011 |

(Continued)

OTHER PUBLICATIONS

International Search Report issued in PCT/EP2015/071934, dated Feb. 1, 2016, 5 pages.

(Continued)

*Primary Examiner* — Elizabeth D Wood
(74) *Attorney, Agent, or Firm* — Albert Shung

(57) ABSTRACT

The present invention relates to a catalyst composition comprising a modified crystalline aluminosilicate of the Framework Type FER having Si/Al framework molar ratio greater than 20 characterized in that in said modified crystalline aluminosilicate the ratio between the strong acid sites and the weak acid sites, S/W, is lower than 1.0 and having the extra framework aluminum (EFAL) content lowered to less than 10 wt % preferably 5 wt % even more preferably less than 2 wt % measured by 27 Al MAS NMR. The present invention further relates to a process for producing olefins from alcohols in presence of said catalyst composition.

8 Claims, 1 Drawing Sheet

(56) References Cited

U.S. PATENT DOCUMENTS

| | | | |
|---|---|---|---|
| 6,103,208 | A | 8/2000 | Ogawa et al. |
| 7,619,103 | B2 * | 11/2009 | Zhang .................. B01J 29/7615 554/125 |
| 7,968,068 | B2 * | 6/2011 | Bull .................... B01D 53/9418 423/239.2 |
| 2005/0101808 | A1 | 5/2005 | Ayoub et al. |
| 2007/0015928 | A1 * | 1/2007 | Zhang .................. B01J 29/7615 554/125 |
| 2014/0296599 | A1 * | 10/2014 | Nesterenko ............. B01J 37/10 585/468 |

FOREIGN PATENT DOCUMENTS

| | | |
|---|---|---|
| WO | 2011113834 A1 | 9/2011 |
| WO | 2013014081 A1 | 1/2013 |

OTHER PUBLICATIONS

Gon Seo et al, "The role of carbonaceous deposits in the skeletal isomerization of 1-butene over ferrierite zeolites", Catalysis Letters, (1996), vol. 41, No. 3-4, pp. 189-194.

D. Rutenbeck et al, "Investigations on the reaction mechanism of the skeletal isomerization of n-butenes to isobutene", Applied Catalysis A: General, (Feb. 2001), vol. 208, No. 1-2, pp. 153-161.

Xu W-Q et al, "Modification of Non-Template Synthesized Ferrierite/Zsm-35 for N-Butene Skeletal Isomerization to Isobutylene", Journal of Catalysis, Academic Press, Duluth, MN, US, (1996), vol. 163, pp. 232-244.

Dazhi Zhang et al, "n-Butanol to iso-butene in one-step over zeolite catalysts", Applied Catalysis A: General, Elsevier Science, Amsterdam, NL, vol. 403, No. 1, (May 28, 2011), pp. 1-11.

Bulánek Roman et al, "Quantitative analysis of IR spectra of carbonylic species in alkali-metal exchanged ZSM-5 and FER zeol", Catalysis Today, (2015), vol. 243, pp. 62-68.

* cited by examiner $^{27}$Al NMR spectra of the various samples.
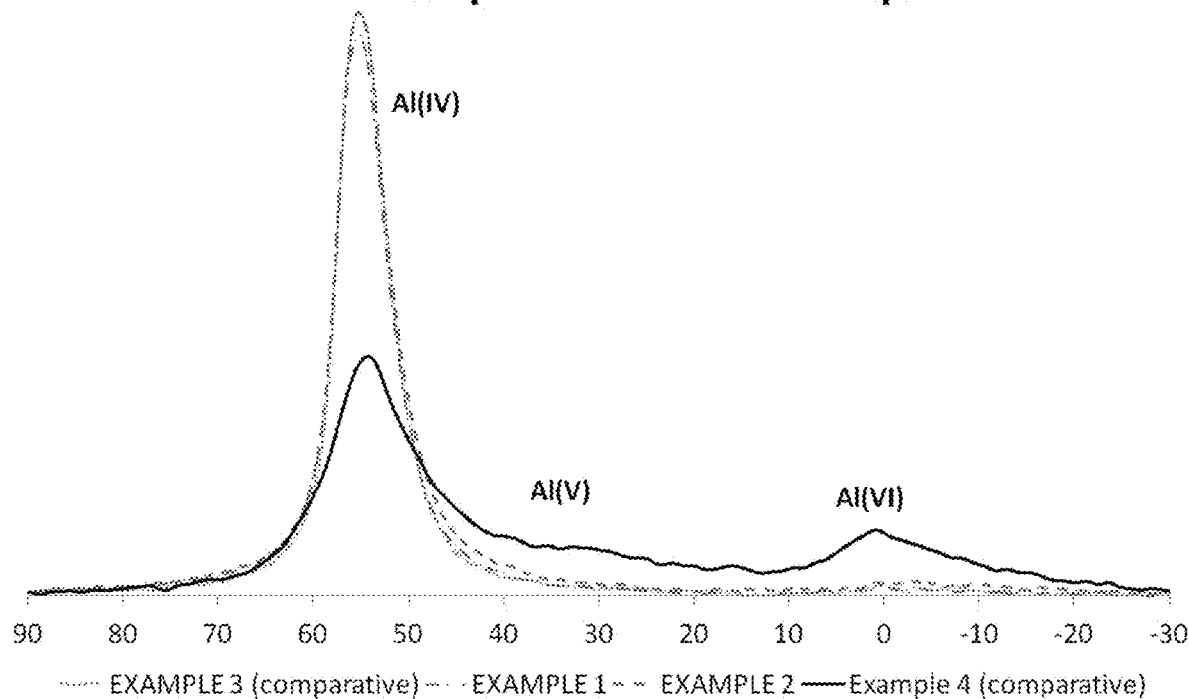

MODIFIED CRYSTALLINE ALUMINOSILICATE FOR DEHYDRATION OF ALCOHOLS

CROSS-REFERENCE TO RELATED APPLICATIONS

This application claims the benefit of PCT/EP2015/071934 filed Sep. 24, 2015, which claims priority from EP 14290289.9 filed Sep. 26, 2014.

TECHNICAL FIELD

The present invention relates generally to the field of dehydration of alcohols on acidic catalysts to make corresponding olefins, preferably of alcohols having at least two carbon atoms for the production of olefins having the same number of carbon atoms as the alcohols. The present invention relates to a catalyst composition comprising a modified crystalline aluminosilicate of the group FER (Framework Type FER) and to a process for the preparation thereof. The present invention also relates to the use of said catalyst composition in a dehydration process of alcohols and to the use of the olefins so-produced in various subsequent processes.

BACKGROUND OF THE INVENTION

The dehydration reactions of alcohols to produce alkenes have been known for a long time. Solid acid catalysts are widely used for alcohol dehydration and the conversion of alcohols therewith is nearly complete. However, in view of the potential downstream applications of olefins, it is of particular importance to limit the amount of secondary products and insure a stable catalyst performance to gain in process efficiency and to save expensive steps of downstream separation/purification as well as to recover the catalyst activity by regeneration.

Dehydration of ethanol was described in WO2011/089235. The process for the dehydration of ethanol to ethylene was carried out in presence of zeolite catalysts and provides an alternative route to ethylene from biobased products if ethanol is obtained by fermentation of carbohydrates.

Dehydration of isobutanol to corresponding olefins brings a perspective route to produce the renewable feedstock for petrochemicals and refining applications. Unfortunately, the direct conversion of isobutanol over a conventional dehydration catalyst, for example on alumina, leads to a product rich in isobutene. Not isobutene but linear butenes are often interesting as feedstock for metathesis, sulfuric acid catalyzed alkylation, oligomerization, oxidative dehydrogenation to butadiene, for the use as a co-polymer or for the integration into the Raffinate I—pool. The definition of Raffinate I shall be found in U.S. Pat. No. 4,282,389 (column 1 lines 41-46). Therefore, one-pot process converting isobutanol to the effluent rich in the linear butenes is sought.

While many skeletal isomerisation catalysts for the conversion of n-butenes into isobutene have been developed, the reverse skeletal isomerisation of isobutene into n-butenes has been rarely mentioned. Among the catalysts being active and selective, there are mostly unidirectional 10-membered ring zeolites. WO2011/113834 relates to the simultaneous dehydration and skeletal isomerisation of isobutanol on acid catalysts. The process discloses the contact of a stream comprising isobutanol with a catalyst able to make such reaction. The catalyst was a crystalline silicate, a dealuminated crystalline silicate, or phosphorus modified crystalline silicate having Si/Al higher than 10; or silicoaluminaphosphate molecular sieve, or a silicated, zirconated or titanated or fluorinated alumina. The conversion of isobutanol was almost complete with selectivity in butenes ranging from 95 wt % to 98 wt %. The selectivity in isobutene was around 41-43%. This document clearly states that steaming at temperature above 400° C. leads to a modification of the acidity of the catalyst and to the removal of aluminum from the crystalline silicate framework. Subsequently, it is necessary to treat the catalyst via a leaching to remove the aluminium and to increase the ratio Si/Al. The steps of steaming and leaching are associated in this document.

However, crystalline silicate catalysts deactivate fast and have limited regenerability. Hence, there is still a need for selective catalysts towards linear olefins and having improved regenerability.

In catalysis letters 41 (1996) 189-194, Gon Seo et al. studied the impact of coke deposits on ferrierite zeolites for the reaction of skeletal isomerization of 1-butene. The ferrierite studied was calcined at 500° C. for 16 h without any other particular treatment aiming at modifying its acidity. This ferrierite has a Si/Al ratio of 21 and it is further covered with coke using a plasma deposition before the reaction of skeletal isomerization of 1-butene is studied.

In WO2013/014081, SUZ-4 is studied for the methanol to olefin reaction. This document discloses the possibility of steaming the catalyst at a temperature of at least 400° C. followed by a leaching i.e. a washing of the steamed solid with an aqueous acid solution. Such treatment are said to increase the Si/Al ratio.

In Applied Catalysis A: General 208 (2001) 153-161, Rutenbeck et al. studied the skeletal isomerization of n-butenes to iso butene. The catalyst studied was a ferrierite having a Si/Al ratio in the range of 20-70. A treatment of the ferrierite with the inorganic acid HCl was performed to obtain the protonic form of the ferrierite.

In the Journal of Catalysis 163, 232-244 (1996), Wen-Qing Xu et al. studied the modification ferrierite for the skeletal isomerization of n-butene. The ferrierite used presents a Si/Al ratio of 8.8. Treatment of the ferrierite also includes steaming at a temperature of at least 550° C. and acidic treatment with HCl or $HNO_3$.

In EP2348005, the use of a ferrierite based catalyst for the dehydration of isobutanol is described. It is disclosed that the ferrierite may be used directly without further treatment or that it may be used once being steamed and dealuminated with an acidic treatment.

In Applied Catalysis A: General 403 (2011) 1-11, Dazhi Zhang et al. described the use of a ferrierite for the conversion of n-butanol to iso-butene. Such ferrierite was calcined at 550° C. but did not undergo any further treatment. The ferrierite used are commercial products: CP914 and CP914C from Zeolyst International.

In U.S. Pat. No. 5,523,510, the use of a acid wash ferrierite based catalyst for the skeletal isomerization of n-olefins to iso-olefins is described. Such acid wash is performed with HCl. In all the examples, the ferrierite is firstly steamed before being acid wash.

The present invention aims at providing catalyst compositions that address the above-discussed drawbacks of the prior art.

BRIEF DESCRIPTION OF THE DRAWING

Figure: The Figure is a spectrum graph depicting Al NMR spectra of Examples 1 through 4.

SUMMARY OF THE INVENTION

In particular, it is an object of the present invention to provide catalyst compositions exhibiting substantially complete once-through conversion of the alcohols to olefins.

Another object of the present invention is to provide catalyst compositions showing good to excellent selectivity to linear olefins, above thermodynamic equilibrium, in simultaneous dehydration and skeletal isomerization reaction of alcohols having at least four carbon atoms.

It is another object of the present invention to provide catalyst compositions that can be easily regenerated.

In a first aspect of the present invention, a catalyst composition is provided. Said catalyst composition comprises a modified crystalline aluminosilicate of the Framework Type FER having Si/Al framework molar ratio greater than 20 characterized in that in said modified crystalline aluminosilicate the ratio between the strong acid sites and the weak acid sites, S/W, is lower than 1.0. The ratio S/W is measured by temperature-programmed desorption of ammonia and is determined by the ratio of the peak area of desorbed ammonia above 340° C. to the peak area of desorbed ammonia below 340° C. Said catalyst composition provides a convenient solution for an alcohol dehydration process exhibiting the required activity and selectivity towards linear olefins preferably of the dehydration of isobutanol (2 methyl propan-1-ol) into n-butenes. It has been observed that selecting a ratio between the strong acid sites and the weak acid sites at the claimed level allows an improvement of the regenerability of said catalyst composition, in particular of said modified crystalline aluminosilicate, while maintaining excellent selectivity towards linear olefins. It has been further observed that the formation of coke in the modified crystalline aluminosilicate is reduced compared to the parent crystalline aluminosilicate having S/W greater than 1.0, and said coke has further lower C/H ratio. It has been further observed that the regenerability of said catalyst composition has been also improved because of the higher hydrothermal stability of the crystalline aluminosilicates having S/W greater than 1.0. Higher hydrothermal stability means better conservation of the aluminium atoms in the framework of the zeolite. Said modified crystalline aluminosilicate is prepared from a crystalline aluminosilicate without steaming, but with a further treatment with an organic acidic medium and/or an organic medium and/or a selective poisoning of strong acid sites of said crystalline aluminosilicate with alkali salts or alkaline earth salts or silver. It has been surprisingly discovered that this treatment with organic acidic medium and/or an organic medium performed on a not steamed crystalline aluminosilicate allows decreasing the quantity of strong acidic sites without creating extra framework aluminium (EFAL). A similar phenomenon is observed with the selective poisoning: no EFAL are formed but the quantity of strong acidic sites is decreased leading to a decrease of the S/W ratio. Steaming leads to the formation of extra framework aluminium (EFAL) that are located inside or outside of the porosity of the crystalline aluminosilicate. Such EFAL species located inside of pore structure block the channels, create duffusion constraints and increase the deactivation rate. The EFAL species located outside of the pores catalyze side-transformations and lead to a loss of shape selectivity of the zeolite framework. That is the reason why the EFAL content should be as low as possible. The EFAL content is lower to less than 25 wt % preferably 15 wt %, preferably lower than 10 wt % even more preferably less than 7 wt % and the most preferred lower than 5 wt % measured by $^{27}$Al MAS NMR. Generally speaking, the speaking a treatment with an mineral acid doesn't allow extracting any Al atoms from framework, only partially dislugged Al-atoms can be washed out. So contrary to treatment with inorganic such as HCl, treatment with an organic acidic medium and/or an organic medium consists of the use of a bulky molecule with chelated function that selectively extracts EFAL located at the outside of the crystal of crystalline aluminosilicate. Strong acidic sites located inside the crystal of crystalline aluminosilicate benefits from the shape selectivity of the crystalline aluminosilicate and do not need to be removed. Such low content of EFAL allows having better selectivity in particular in the case of the conversion of isobutanol into n-butenes while maintaining the conversion at a high level.

In a preferred embodiment, said modified crystalline aluminosilicate is prepared without being calcined or with a thermal treatment or calcinations at temperature lower than 600° C. preferably 550° C., most preferably 500° C. and with a temperature increase of less than 10° C./min, preferably less than 1° C./min, the most preferably at 0.5° C./min, for a period of at least 30 min, preferably at least 2 h and at most 48 h and under a gas flow containing at most 1000 ppm volume of water measured at the inlet of the calcination reactor. Indeed, more stringent calcination conditions would lead to the formation of extra framework aluminium (EFAL) because of the presence of interstitial water inside the crystalline aluminosilicate leading to a partial steaming but without bringing any advantages in terms of conversion or selectivity. The thermal treatment applied in the object of the present invention is such that steaming conditions are avoided, steaming conditions being defined as a treatment performed under an atmosphere containing from 5 to 100% vol of steam the rest being constituted of an inert gas and performed at temperature ranging from 425° C. to 870° C. under atmospheric pressure. Steaming is also generally performed during time period ranging from 30 min to 50 hours. When a steaming is performed, the amount of tetrahedral aluminium in the crystalline aluminosilicate is reduced and EFAL are formed. Steaming can be alternatively defined as a treatment of the crystalline aluminosilicate under steam leading to an increase of the EFAL content of at least 5% wt measured via $^{27}$Al NMR.

In a preferred embodiment, the modified crystalline aluminosilicate is a modified crystalline ferrierite.

In a second aspect of the present invention a process for the preparation of the catalyst composition is provided. Said process comprises the steps of:

(A) providing a crystalline aluminosilicate of the Framework Type FER having Si/Al framework molar ratio greater than or equal to 20, and (B) treating said crystalline aluminosilicate to form a modified crystalline aluminosilicate with one or more of the following steps:

i. Not performing any steaming on said crystalline aluminosilicate and performing optionally a calcination at a temperature lower than 600° C., preferably 550° C., most preferably 500° C. and with a temperature increase of less than 10° C./min, preferably less than 1° C./min, the most preferably at 0.5° C./min, for a period of at least 30 min, preferably at least 2 h and at most 48 h and under a gas flow containing at most 1000 ppm volume of water measured at the inlet of the calcination reactor ii. treating the product obtained at step i.) with an organic acidic medium or an organic medium;

iii. selectively poisoning strong acid sites of the product obtained at step i.) or ii.) by adding a solution comprising alkali salts or alkaline earth salts, so that the weight percent of alkali or alkaline earth on the catalyst composition is of at least 0.1% weight, more preferably at least 1% weight, most preferably at least 5% weight measured by chemical analysis with the method ASTM UOP961-12; said alkaline earth being preferably sodium at a preferable content of 1% wt.

(C) wherein said modified crystalline aluminosilicate obtained with said treatment (B) has the invention.

In a third aspect of the present invention, a dehydration process of alcohols for the production of a mixture of olefins is provided. Said process comprises the steps of:

(a) providing an alcohol having at least two carbon atoms, and preferably at most 7 carbon atoms, or mixture thereof with the proviso that the alcohols contained in the mixture have the same number of carbon atoms, or optionally the alcohols contained in the mixture have a different number of carbon atoms, (b) introducing in a reactor a stream (S1) comprising said alcohol, and optionally water and optionally an inert component, (c) contacting said stream (S1) with a catalyst composition according to the present invention under conditions suitable for producing a mixture of corresponding olefins having the same number of carbon atoms as the alcohol, and (d) recovering from said reactor a stream (S2), optionally removing water and the inert component and if any unconverted alcohol and other oxygenated compounds to get a mixture of olefins having the same number of carbon atoms as said alcohol.

In a particular embodiment, step (c) may also be carried out under conditions suitable for producing a mixture of corresponding olefins having the same number of carbon atoms as the alcohol, and suitable for simultaneous skeletal isomerisation, for example when the alcohol has at least four carbon atoms.

Preferably, said alcohol may be selected from $C_2$-$C_7$ alkyl substituted by one hydroxyl group or mixture thereof with the proviso that the alcohols contained in the mixture have the same number of carbon atoms. Preferably, said mixture of alcohols may comprise alcohols having at least three carbon atoms, more preferably at most seven carbon atoms. For example, said alcohol may be a mixture of isobutanol and n-butanol.

In particular, the present process is suitable for the production of olefins from alcohols having two, three or four carbon atoms, preferably for the production of linear butenes from isobutanol. The present process allows a substantially complete once-through conversion of alcohols to corresponding olefins having the same number of carbon atoms by eliminating or poisoning the unselective catalytic acid sites.

DETAILED DESCRIPTION OF THE INVENTION

The present invention relates to a catalyst composition comprising a modified crystalline aluminosilicate of the Framework Type FER having Si/Al framework molar ratio greater than 20 characterized in that in said modified crystalline aluminosilicate the ratio of strong acid sites to weak acid sites, S/W, is lower than 1.0. The ratio S/W is measured by temperature-programmed desorption of ammonia and is determined by the ratio of the peak area of desorbed ammonia above 340° C. to the peak area of desorbed ammonia below 340° C. Said S/W ratio being obtained with one of the following treatment: either treatment with an organic acidic medium and/or an organic medium and/or a selective poisoning strong acid sites of the crystalline aluminosilicate with alkali salts or alkaline earth salts or silver performed on crystalline aluminosilicate that has not been steamed. Additionally in said modified crystalline aluminosilicate the extra framework aluminum (EFAL) content is lowered to less than 10 wt % preferably 7 wt % even more preferably less than 2 wt % measured by $^{27}Al$ MAS NMR.

In a preferred embodiment, the calcination procedure is performed to burn organic component that may be present on the crystalline aluminosilicate but under conditions avoiding the formation of EFAL. In particular, at the inlet of the calcinations reactor, the calcination gas should contain less than 1000 wt ppm of water. Therefore even if the crystalline aluminosilicate contains interstitial water, the presence of water inside the calcinations reactor is low enough to avoid a partial steaming of the crystalline aluminosilicate. During the optional calcinations, the crystalline aluminosilicate may be under the NH4 form, the Na, K or H-forms. The calcination can be performed under atmospheric pressure or alternatively at a pressure up to 8 barg. The calcination gas may contains inert components such as for instance N2, Ar, He, CO2, or other species such as for instance natural gas components or CO, N2O which are not inert under the calcination conditions but do not lead to the deposition of any molecules such as coke on the crystalline aluminosilicate. The calcination may be alternatively be performed under depleted air or the calcination gas may contains below 10 wt % of oxygen or preferably below 5 wt % or even below 1 wt % of oxygen in order to avoid the thermal runaway when organic molecules are burned during calcination.

In a preferred embodiment, the Framework Type FER is a crystalline aluminosilicate containing advantageously at least one 10 members ring into the structure based on T-atoms, i.e. on the Al and Si atoms contained in said ring. The family of Framework Type FER includes Ferrierite, [B—Si—O]-FER, [Ga—Si—O]-FER, [Si—O]-FER, [Si—O]-FER, FU-9, ISI-6, Monoclinic ferrierite, NU-23, Sr-D; ZSM-35

In a preferred embodiment, the modified crystalline aluminosilicate of the Framework Type FER is selected from Ferrierite, FU-9, Nu-23, ISI-6, ZSM-35 and SUZ-4. Preferably, the modified crystalline aluminosilicate of the Framework Type FER is Ferrierite.

In another preferred embodiment, said organic acidic medium and/or said organic medium is chosen among citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyl ethylene diamine triacetic acid, ethylene diamine tetracetic acid, trichloroacetic acid trifluoroacetic acid methansulfonic or a salt of such an acid (e.g. the sodium salt) or a mixture of two or more of such acids or salts. Inorganic acid such as nitric acid or halogenic acids are not encompassed in the meaning of organic acidic medium. Organic medium shall encompass any organic molecule able to form a complex with aluminium and preferably forms a water-soluble complex with aluminium in order to remove EFAL which are non selective strong acidic sites. A particularly preferred complexing agent may comprise an amine, preferably ethylene diamine tetraacetic acid (EDTA) or a salt thereof, in particular the sodium salt thereof. The term "organic medium" shall encompass also organic acidic medium but not only. The man skilled in the art can recognize the organic medium able to remove the EFAL from a crystalline aluminosilicate. As a guidance, it may be put forward that said organic medium refers to organic molecule able to form a complex with aluminium and preferably forms a water-soluble complex with aluminium in order to remove EFAL i.e. in order to remove at least 5 wt % preferably 10 wt % of the EFAL present on the crystalline aluminosilicate.

As mentioned above, the Si/Al framework molar ratio of the modified crystalline aluminosilicate may be greater than 20, preferably greater than 21, more preferably greater than 22, most preferably greater than 25. Preferably, the Si/Al framework molar ratio of the modified crystalline aluminosilicate may be at most 150, preferably at most 100, more preferably at most 75. In a preferred embodiment, the Si/Al framework molar ratio of the modified crystalline aluminosilicate may range from 11 to 150, preferably from 15 to 100, more preferably from 20 to 100, even more preferably from 20 to 75, and in particular from 25 to 50. Advantageously the modified crystalline aluminosilicate shows a high crystallinity of its zeolite phase, said crystallinity being similar to the crystallinity of the parent zeolite before modification. A similar crystallinity is evidenced via the X ray diffraction patterns (less than 20% of difference measured on the area below the X ray curves).

In a preferred embodiment, the ratio of strong acid sites to weak acid sites, S/W, in said modified crystalline aluminosilicate may be lower than 0.99, preferably lower than 0.98, more preferably lower than 0.97, most preferably lower than 0.96. In a preferred embodiment, the ratio of strong acid sites to weak acid sites, S/W, may also be greater than 0.1, preferably greater than 0.2, more preferably greater than 0.25, most preferably greater than 0.3. In a specific embodiment, the ratio of strong acid sites to weak acid sites, S/W, may be lower than 0.9, preferably lower than 0.8.

In a preferred embodiment, said modified crystalline aluminosilicate has content in redox metals or cations thereof lower than 1000 wt ppm, said metals belonging to one of columns 3 to 12 of the Periodic Table. Preferably, said metals are Fe, Co, Ni, Cu, Mo, Mn, Ti, Zn, V, Cr, Ru, Rh, Cd, Pt, Pd, Au, Zr. Preferably, said modified crystalline aluminosilicate has content in metals or cations thereof as defined above lower than 500 wt ppm, more preferably lower than 200 wt ppm, most preferably lower than 100 wt ppm, in particular lower than 50 wt ppm being measured with the method ASTM UOP961-12.

In another specific embodiment, the catalyst composition may comprise a binder, preferably an inorganic binder. The binder is selected so as to be resistant to the temperature and other conditions employed in the dehydration process of the invention. The binder is an inorganic material selected from clays, silica, metal silicate, metal oxides (such as $ZrO_2$), alumina, aluminophosphate binders, in particular, stoichiometric amorphous aluminophosphate or gels including mixtures of silica and metal oxides. It is desirable to provide a catalyst having good crush strength. This is because in commercial use, it is desirable to prevent the catalyst from breaking down into powder-like materials. Such clay or oxide binders have been employed normally only for the purpose of improving the crush strength of the catalyst. Preferably, said binder is selected from the group consisting of clays, alumina, silica-alumina, silica, titania, aluminophosphate, titania-silica. A particularly preferred binder for the catalyst composition of the present invention is silica. The relative proportions of the finely divided modified crystalline aluminosilicate material and the inorganic oxide matrix of the binder can vary widely. Typically, the binder content may range from 5 to 95% by weight, more typically from 20 to 85% by weight, based on the weight of the catalyst composition. By adding a binder to the catalyst composition, this latter may be formulated into pellets, extruded into other shapes, or formed into spheres or a spray-dried powder.

The modified crystalline aluminosilicate may be in H-form. The H-form of a modified crystalline aluminosilicate of the Framework Type FER means that it comprises oxygen atoms bonded to one aluminium atom and one silicon atom, and which is protonated with a hydrogen atom, resulting in the following sequence —[—Al—O(H)—Si—]—. In the present invention, the modified crystalline aluminosilicate may be essentially under H-form, which means containing less than 1000 wt ppm of the total amount of the alkali ions and the alkaline earth ions. In another embodiment, the modified crystalline aluminosilicate is partly under H-form. It means that in said modified crystalline aluminosilicate part of the hydrogen atoms bonded to oxygen atoms in the following sequence —[—Al—O(H)—Si—]— is substituted by metallic ions, preferably alkali ions, alkaline earth ions or silver ions. In a preferred embodiment, the modified crystalline aluminosilicate comprises the sequences —[—Al—O(H)—Si—]— and —[—Al—O(X)—Si—]— wherein X is alkali ions, alkaline earth ions or silver ions, the sequence —[—Al—O(X)—Si—]— representing less than 75% wt based on the total amount of sequences —[—Al—O(H)—Si—]— and —[—Al—O(X)—Si—]— in said modified crystalline aluminosilicate, preferably the sequence —[—Al—O(X)—Si—]— represents less than 50% wt, more preferably less than 25% wt, and preferably at least 1% wt, more preferably at least 5% wt, most preferably at least 10% wt being measured via solid-state $^{29}Si$ NMR and/or with the method ASTM UOP961-12. Preferably, the alkali ions or alkaline earth ions may be Na, K, Cs, Li, Mg or Ca being measured via chemical analysis with the method ASTM UOP961-12.

Alternatively, the modified crystalline aluminosilicate may have content in one of the elements selected from the group consisting of lithium, sodium, cesium, magnesium, calcium, potassium and silver, independently from one another, ranging from 10 to 10000 wt ppm, preferably ranging from 10 to 5000 wt ppm, more preferably ranging from 10 to 3000 wt ppm, most preferably ranging from 10 to 2000 wt ppm. Said above mentioned compositions are measured via chemical analysis with the method ASTM UOP961-12.

In a preferred embodiment, after having been used in a catalytic process, for example in a process of dehydration of alcohols for the production of olefins according to the present invention, the catalyst composition may have on its external surface, or within its pores, coke residues comprising paraffins, oligomers or aromatics hydrocarbons. The density of the coke residue may be characterized by the carbon to hydrogen weight ratio C/H in said catalyst composition and may be determined by CHN or by other techniques, for example nuclear magnetic resonance (NMR). Such ratio may be determined on spent catalyst composition, i.e. on catalyst composition which has been used in a process according to the present invention, in particular on catalyst composition which has been in contact with an alcohol having at least two carbon atoms under conditions suitable for dehydration of said alcohol and production of the corresponding olefin having the same number of carbon atoms as the alcohol. Lower C/H ratio on the spent catalyst corresponds to softer coke depositions. It was observed that the catalysts with softer coke were more prone to regeneration. Hence, the carbon to hydrogen weight ratio, C/H, in said spent catalyst composition may be lower than 5.5, preferably lower than 4.5, more preferably lower than 4.0. Preferably the carbon to hydrogen weight ratio C/H, in said catalyst composition may be greater than 0.5, more preferably greater than 1.5, most preferably greater than 2.0. Preferably, according to the conditions described herein, said catalyst composition may have a carbon to hydrogen weight ratio, C/H, ranging from 0.5 to 5.5, preferably from 1.5 to 5.0, more preferably from 2.0 to 4.5. In a particular embodiment, the above-mentioned ranges or values of the carbon to hydrogen weight ratio, C/H, may be observed when the alcohol was contacted with the present catalyst composition at pressure from 0.1 to 10 barg, at temperatures between 100 and 500° C., and with an alcohol weight hour space velocity (WHSV) from 0.1 to 20 h$^{-1}$ in presence, or not, of steam or other diluents ($N_2$, He, Ar). In a particular embodiment, when the catalyst composition consists of a modified crystalline aluminosilicate as defined herein, the carbon to hydrogen weight ratio C/H, is determined on the spent modified crystalline aluminosilicate, i.e. on the modified crystalline aluminosilicate which has been in contact with an alcohol having at least two carbon atoms under conditions suitable for dehydration of alcohols and production of the corresponding olefins. Said spent modified crystalline aluminosilicate may have a carbon to hydrogen weight ratio, C/H, as mentioned above.

In a second aspect of the present invention, a process for the preparation of the catalyst composition is provided. Said process comprises the steps of:
  (A) providing a crystalline aluminosilicate of the Framework Type FER having Si/Al molar ratio greater than or equal to 20, and
  (B) treating said crystalline aluminosilicate to form a modified crystalline aluminosilicate with one or more of the following steps:
    i. Not performing any steaming
    ii. treating the product obtained at step i.) with an organic acidic medium or an organic medium;
    iii. selectively poisoning strong acid sites of the product obtained at step i.) or ii.) by adding a solution comprising alkali salts or alkaline earth salts, so that the weight percent of alkali or alkaline earth on the catalyst composition is of at least 1% weight, more preferably at least 5% weight, most preferably at least 10% weight measured by chemical analysis with the method ASTM UOP961-12; said alkaline earth being preferably sodium at a preferable content of 1% wt.
  (C) wherein said modified crystalline aluminosilicate obtained with said treatment (B) has the characteristics of any of the characteristic described above.

In a preferred embodiment, an optional calcination is performed before step ii.) said calcination being performed at a temperature lower than 600° C., preferably 550° C., most preferably 500° C. and with a temperature increase of less than 10° C./min, preferably less than 1° C./min, the most preferably at 0.5° C./min, for a period of at least 30 min, preferably at least 2 h and at most 48 h and under a gas flow containing at most 1000 ppm volume of water measured at the inlet of the calcination reactor.

Preferably, according to the present process for the preparation of the present catalyst composition the treatment carried out in step (B) allows the preparation of a modified crystalline aluminosilicate of the Framework Type FER wherein the Si/Al framework molar ratio is increased and the number of strong acid sites measured by TPD of ammonia therein is decreased compared to said crystalline aluminosilicate of the Framework Type FER provided in step (A), i.e. before treatment. Advantageously the modified crystalline aluminosilicate shows a high crystallinity of its zeolite phase, said crystallinity being similar to the crystallinity of the parent zeolite before modification. A similar crystallinity is evidenced via the X ray diffraction patterns (less than 20% of difference measured on the area below the X ray curves). The treatment of step (B) allows decreasing the EFAL content, which leads to a lower S/W ratio.

In a preferred embodiment, the crystalline aluminosilicate of the group Framework Type FER provided in step (A) is selected from Ferrierite, FU-9, Nu-23, ISI-6, ZSM-35 and SUZ-4. Preferably, the crystalline aluminosilicate of the Framework Type FER is Ferrierite. Preferably, the crystalline aluminosilicate provided in step (A) has a ratio of strong acid sites to weak acid sites greater than or equal to 1.0.

Preferably, the modified crystalline aluminosilicate formed in step (B) may have Si/Al framework molar ratio greater than 20, preferably greater than 21, more preferably greater than 22, most preferably greater than 25. Preferably, the Si/Al framework molar ratio of the modified crystalline aluminosilicate may be at most 150, preferably at most 100, more preferably at most 75. In a preferred embodiment, the Si/Al framework molar ratio of the modified crystalline aluminosilicate may range from 11 to 150, preferably from 15 to 100, more preferably from 20 to 100, even more preferably from 20 to 75, most preferably from 25 to 50 being measured via solid-state $^{29}$Si NMR.

In a preferred embodiment, the modified crystalline aluminosilicate may have lamellar or not crystal morphology. The size of the smallest crystal dimension may be greater than 0.1 μm.

In a preferred embodiment, the modified crystalline aluminosilicate formed in step (B) may have a ratio of strong acid sites to weak acid sites, S/W, lower than 1.0, preferably lower than 0.99, more preferably lower than 0.98, even more preferably lower than 0.97, most preferably lower than 0.96. In a specific embodiment the modified crystalline silicate formed in step (B) may have a ratio of strong acid sites to weak acid sites, S/W, lower than 0.8, preferably lower than 0.7. In a preferred embodiment, the modified crystalline aluminosilicate formed in step (B) may have a ratio of strong acid sites to weak acid sites, S/W, greater than 0.1, preferably greater than 0.2, more preferably greater than 0.25, most preferably greater than 0.3. Preferably the modified crystalline aluminosilicate formed in step (B) may have an extra framework aluminum (EFAL) content is lower than 25 wt % preferably 15 wt %, preferably lower than 10 wt % even more preferably less than 5 wt % and the most preferred lower than 2 wt % measured by $^{27}$Al MAS NMR. The $^{27}$Al MAS NMR is performed on hydrated samples over a night in presence of saturated aqueous solution of KCl. Samples may be measured with the help of a MAS 4 mm probe for instance on a Bruker DRX (500 MHz) spectrometer. Rotation speed of the sample may be of 15000 Hz. The EFAL content is then calculated with the ratio of the area of the peak of Al(VI) at 0 ppm+Al(V) at 35 ppm relative to total area of the peak of the spectrum obtained by deconvolution (i.e. the total area of the peak of Al(VI) at 0 ppm+Al(V) at 35 ppm+Al(IV) at 55 ppm).

Any of the treatment steps (i) to (iii) may be repeated until the modified crystalline aluminosilicate so-formed reaches the required values with respect to the Si/Al framework molar ratio and with respect to the ratio of strong to weak acid sites. Two or more of the treatment steps (i) to (iii) may be combined together to form the modified crystalline aluminosilicate as defined herein. For example, step (i) or (iii) may be subsequently combined with step (ii) to enhance the properties of the modified crystalline aluminosilicate, in particular of the modified crystalline ferrierite, and of the catalyst composition comprising the same in terms of selectivity, activity or regenerability.

The treatment of said crystalline aluminosilicate of the Framework Type FER in an acidic medium may comprise the step of contacting said crystalline aluminosilicate of the Framework Type FER, provided in step (A), with a solution, preferably an aqueous solution, containing one or more organic medium or compounds, each organic medium or compound comprising one or more —$CO_2H$, —$SO_3H$ or —$SO_4H$ groups or salts thereof, preferably two or more —$CO_2H$, —$SO_3H$ or —$SO_4H$ groups or salts thereof. Without willing to be bound by theory this step may allow decreasing acid sites density and removing non-selective acid sites in said crystalline aluminosilicate. Preferably, the solution contains one or more organic medium or compounds, each comprising one or more —$CO_2H$ groups or salts thereof, preferably two or more —$CO_2H$ groups or salts thereof. More preferably, the solution contains one or more organic medium or compounds selected from the group consisting of citric acid, maleic acid, ethylenediaminetetracetic acid, tartaric acid, fumaric acid, oxalic acid, malonic acid, succinic acid, adipic acid, glutaric acid or itaconic acid, phtalic acid, isophtalic acid, nitrilotriacetic acid, hydroxyethylenediaminetriacetic acid, or salts thereof or mixture thereof. More preferably, said solution comprises citric acid, maleic acid, tartaric acid or ethylenediaminetetracetic acid methansulfonic or salts thereof or mixture thereof. The concentration in each one or more organic medium or compounds in said solution may range from $1.10^{-4}M$ to 10M, preferably from $1.10^{-3}M$ to 1M. Step (i) may be carried out at temperature ranging from 10° C. to 110° C., preferably from 20° C. to 80° C., preferably from 30 min to 24 h, more preferably from 1 h to 12 h.

Preferably, in said solution, said one or more organic medium or compounds may be under the form of water soluble salt, preferably sodium, potassium, magnesium, calcium, lithium, cesium or silver salt or mixture thereof. When a salt of said one or more organic medium or compounds is used, the amount and the concentration of the solution comprising the same can be adjusted such that, in the so-formed modified crystalline aluminosilicate, the sequence —[—Al—O(X)—Si—]— wherein X is alkali, alkaline earth or silver ions, represents at most 75% wt of the total amount of sequences —[—Al—O(X)—Si—]— and —[—Al—O(X)—Si—]—, preferably at most 50% wt, more preferably at most 25% wt, and preferably at least 1% wt, more preferably at least 5% wt, most preferably at least 10% wt being measured via solid-state $^{29}Si$ NMR.

Preferably, said crystalline aluminosilicate is selected to have initially a low content of EFAL i.e. a content of EFAL lower than 15% wt preferably lower than 10% wt even more preferably lower than 5% wt.

The step (ii) of applying ion exchange to the crystalline aluminosilicate to form the modified crystalline aluminosilicate may be carried out by contacting said crystalline aluminosilicate with a solution containing one or more inorganic salts such as inorganic ammonium salt, inorganic calcium salt, inorganic lithium salt, inorganic sodium salt, inorganic potassium salt, inorganic magnesium salt or inorganic silver salt. Inorganic salt may be salt of nitric acid, halogenic acid, sulfuric acid, sulfurous acid, nitrous acid or mixture thereof, preferably nitric acid or halogenic acid or mixture thereof. The concentration of each inorganic salt and of the organic acidic medium and/or of the organic medium in said solution may range from $1.10^{-4}M$ to 10M, preferably from $1.10^{-3}M$ to 1M. Step (ii) may be carried out at temperature ranging from 10° C. to 110° C., preferably from 20° C. to 80° C., preferably for 30 min to 24 h, more preferably for 1 h to 10 h. Preferably, the solution may contain ammonium salt, calcium salt or lithium salt of nitric acid or halogenic acid.

The step (iii) of selectively poisoning strong acid sites of the crystalline aluminosilicate to form the modified crystalline aluminosilicate may be carried out by impregnating said crystalline aluminosilicate of step (A) with an aqueous solution containing alkali ions or alkaline earth ions, preferably sodium, lithium, potassium, cesium, magnesium or calcium ions or mixture thereof. The amount and the concentration of said aqueous solution containing alkali ions or alkaline earth ions can be adjusted such that in the so-formed modified crystalline aluminosilicate, the sequence —[—Al—O(X)—Si—]— wherein X is alkali ions or alkaline earth ions, as defined above, represents at most 75% wt of the total amount of sequences —[—Al—O(X)—Si—]— and —[—Al—O(X)—Si—]—, preferably at most 50% wt, more preferably at most 25% wt, and preferably at least 1% wt, more preferably at least 5% wt, most preferably at least 10% wt being measured via a combination of solid-state $^{29}Si$ NMR with elemental analysis. In particular, the concentration of said solution ranges from $1.10^{-4}M$ to 10M, preferably from $1.10^{-3}M$ to 5M. Step (iii) may be carried out at temperature ranging from 10° C. to 100° C., preferably from 20° C. to 30° C. The suspension or solution formed by contacting said crystalline aluminosilicate of step (A) with an aqueous solution containing alkali ions or alkaline earth ions may be further heated at temperature ranging from 50° C. to 100° C., for a period ranging from 1 h to 24 h.

In a preferred embodiment, the process for the preparation of the catalyst composition may further comprise, subsequently to step (B), the step of drying said modified crystalline aluminosilicate formed in step (B) at temperature ranging from 50° C. to 200° C. for a period ranging from 30 min to 24 h, preferably from 1 h to 15 h. In a further preferred embodiment, the present process may further comprise the step of calcining said modified crystalline aluminosilicate formed in step (B) at temperature ranging from 200° C. to 920° C. for a period ranging from 1 h to 48 h. Preferably, the calcining step is carried out subsequently to the drying step.

In a specific embodiment, the catalyst composition according to the present invention may comprise a binder, preferably an inorganic binder. Said binder may be mixed to the modified crystalline aluminosilicate or to the crystalline aluminosilicate, i.e. prior or subsequently to step (B) of the present process. Typically, the binder and the crystalline aluminosilicate, modified or not, are mixed together by a mixing process. In such a process, the binder, for example silica, in the form of a gel is mixed with the crystalline aluminosilicate, modified or not. The resultant mixture is extruded into the desired shape, for example cylindrical or multi-lobe bars. Spherical shapes can be made in rotating granulators or by oil-drop technique. Small spheres can further be made by spray-drying a catalyst-binder suspension. Thereafter, the extruded material containing the binder and the crystalline aluminosilicate, modified or not, is calcined in air or an inert gas, typically at a temperature of from 200 to 900° C. for a period of from 1 to 48 hours. Preferably, said binder is selected from the group consisting of clays, alumina, silica-alumina, silica, titania, aluminophosphate, titania-silica. Hence, according to the present process, the crystalline aluminosilicate provided in step (A) may encompass the extruded material containing the binder and the crystalline aluminosilicate as described herein.

In a third aspect, the present invention provides a dehydration process of alcohols for the production of a mixture of olefins comprising the steps of:
  (a) providing an alcohol having at least two carbon atoms, and preferably at most 7 carbon atoms, or mixture thereof with the proviso that the alcohols contained in the mixture have the same number of carbon atoms,
  (b) introducing in a reactor a stream (S1) comprising said alcohol, and optionally water and optionally an inert component,
  (c) contacting said stream (S1) with a catalyst composition according to the present invention under conditions suitable for producing a mixture of olefins having the same number of carbon atoms as the alcohol,
  (d) recovering from said reactor a stream (S2), optionally removing water and the inert component and if any unconverted alcohol to get a mixture of olefins having the same number of carbon atoms as the alcohol.

In a particular embodiment, step (c) may also be carried out under conditions suitable for producing a mixture of corresponding olefins having the same number of carbon atoms as the alcohol, and suitable for simultaneous skeletal isomerisation, for example when the alcohol is a mixture of alcohol having at least four carbon atoms.

Preferably, the alcohol has at least two carbon atoms and at most 7 carbon atoms. Preferably, the alcohols are provided from biomass fermentation or biomass gasification to syngas followed by a modified Fischer-Tropsch synthesis. Preferably, said alcohol may be selected from $C_2$-$C_7$ alkyl substituted by one hydroxyl group or mixture thereof with the proviso that the alcohols contained in the mixture have the same number of carbon atoms. Whenever the term "substituted" is used in the present invention, it is meant to indicate that one or more hydrogen on the atom indicated in the expression using "substituted" is replaced with a selection from the indicated group, provided that the indicated atom's normal valence is not exceeded, and that the substitution results in a chemically stable compound, i.e. a compound that is sufficiently robust to survive isolation to a useful degree of purity from a reaction mixture. The term "alkyl" by itself or as part of another substituent refers to a hydrocarbyl radical of formula $C_nH_{2n+1}$ wherein n is a number between 2 and 7.

Preferably, the alcohol may be ethanol, propanol, isopropanol, 1-butanol, 2-butanol, isobutanol, pentan-1-ol, 3-Methylbutan-1-ol, 2-Methylbutan-1-ol, 2,2-Dimethylpropan-1-ol, pentan-3-ol, Pentan-2-ol, 3-Methylbutan-2-ol, 2-Methylbutan-2-ol, 1-hexanol, 2-hexanol, 3-hexanol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol or 2-ethylbutan-1-ol, or mixture thereof with the proviso that the mixture contains alcohols having the same number of carbon atoms or optionally presenting a different number of carbon atoms. For example, a mixture of butanol comprises two or more of the following alcohols: 1-butanol, 2-butanol, isobutanol. A mixture of pentanol comprises two or more of the following alcohols: pentan-1-ol, 3-methylbutan-1-ol, 2-methylbutan-1-ol, 2,2-dimethylpropan-1-ol, pentan-3-ol, pentan-2-ol, 3-methylbutan-2-ol, 2-methylbutan-2-ol. A mixture of hexanol comprises two or more of the following alcohols: 1-hexanol, 2-hexanol, 3-hexanol, 2-methylpentan-1-ol, 3-methylpentan-1-ol, 4-methylpentan-1-ol, 2-methylpentan-2-ol, 3-methylpentan-2-ol, 4-methylpentan-2-ol, 2-methylpentan-3-ol, 3-methylpentan-3-ol, 2,2-dimethylbutan-1-ol, 2,3-dimethylbutan-1-ol, 3,3-dimethylbutan-1-ol, 2,3-dimethylbutan-2-ol, 3,3-dimethylbutan-2-ol or 2-ethylbutan-1-ol. More preferably, the alcohol may be selected from C2-C4 alkyl substituted by one hydroxyl group or mixture thereof with the proviso that the alcohols contained in the mixture have the same number of carbon atoms. Advantageously, the invention is of interest for ethanol, 1-propanol, isopropanol, 1-butanol, 2-butanol, isobutanol or mixture thereof with the proviso that the mixture contains alcohols having the same number of carbon atoms. In particular, a mixture of butanol is used, preferably isobutanol is used.

The inert component is any component provided that there is no adverse effect on the catalyst composition, preferably on the modified crystalline aluminosilicate, in particular on the modified crystalline ferrierite. Because the dehydration is endothermic the inert component can be used to bring energy. By way of examples the inert component is selected among water, saturated hydrocarbons having up to 10 carbon atoms, naphtenes, nitrogen and $CO_2$. An example of inert component can be any individual saturated compound, a synthetic mixture of the individual saturated compounds as well as some equilibrated refinery streams like straight naphtha, butanes. Advantageously it is a saturated hydrocarbon or a mixture of saturated hydrocarbons having from 3 to 7 carbon atoms, more advantageously having from 4 to 6 carbon atoms and is preferably pentane. The weight proportions of respectively alcohols, water and inert component are, for example, 5-100/0-95/0-95 (the total being 100). Although the reactant could comprise less than about 5% water by weight relative to the weight of the water plus alcohol, it is preferred that the reactant comprise at least about 5% water. In a more specific embodiment, the reactant comprises from about 5% to about 80% water by weight relative to the weight of the water plus alcohol.

The dehydration reactor can be a fixed bed reactor (radial, isothermal, adiabatic etc), a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using several reactors in series of equal or different sizes or a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

The pressure in the reactor for step (c) can be any pressure but it is more economical to operate at moderate pressure. By way of example the pressure of the reactor may range from 0.5 to 30 bars absolute (50 kPa to 3 MPa), advantageously from 0.5 to 10 bars absolute (50 kPa to 1 MPa), advantageously from 0.5 to 9 bars absolute (50 kPa to 0.9 MPa). Advantageously, the partial pressure of the alcohol is advantageously lower than 5 bars absolute (0.5 MPa) and more advantageously from 0.5 to 4 bars absolute (0.05 MPa to 0.4 MPa), preferably lower than 3.5 bars absolute (0.35 MPa) and more preferably lower than 2 bars absolute (0.2 MPa).

The temperature of the dehydration reactor may range advantageously from 200° C. to 500° C., more advantageously from 220° C. to 500° C. and preferably from 230° C. to 450° C. These reaction temperatures refer substantially to average catalyst bed temperature. Dehydration is an endothermic reaction and requires the input of reaction heat in order to maintain catalyst activity sufficiently high and shift the thermodynamic equilibrium to sufficiently high conversion levels. In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds. In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

The dehydration reaction (steps (b) and/or (c)) may be carried out with an alcohol weight hour space velocity ranging from 0.1 h−1 to 20 h−1, preferably from 0.5 h−1 to 10 h−1, more preferably from 1 h−1 to 9 h−1.

The stream (S2) of step (d), comprises essentially water, olefin, the inert component (if any) and unconverted alcohol. Said unconverted alcohol is supposed to be as less as possible. The olefin is recovered by usual fractionation means. Advantageously the inert component, if any, is recycled in the stream (S1) as well as the unconverted alcohol, if any.

In another embodiment, a solution containing one or more organic medium or compounds, each medium or compound comprising one or more —$CO_2H$, —$SO_3H$ or —$SO_4H$ groups or salts thereof as defined above may also be added during the use of the present catalyst composition in a process for dehydration of alcohol as disclosed herein. In this respect, the amount of said one or more organic medium or compounds each medium or compound comprising one or more —$CO_2H$, —$SO_3H$ or —$SO_4H$ groups or salts thereof, can be adjusted to compensate for changes in feed residence time, the feed composition and loss of catalyst activity through deactivation. In still another embodiment, the reaction temperature at which the process for dehydration of alcohol is carried out can be increased to maximise conversion while adding said one or more organic compounds to the feed or while said one or more organic compounds are already present in the feed.

In a preferred embodiment, said process for the production of olefins from alcohols may further comprise the step of recovering and regenerating the catalyst composition obtained at the end of step (d). In particular, the catalyst composition obtained at the end of step (d) has a carbon to hydrogen weight ratio, C/H, lower than 5.5, preferably lower than 4.5, more preferably lower than 4.0. Preferably the carbon to hydrogen weight ratio C/H, in said catalyst composition, obtained at the end of step (d), may be greater than 0.5, more preferably greater than 1.5, most preferably greater than 2.0. Hence, said catalyst composition obtained at the end of step (d) may have a carbon to hydrogen weight ratio, C/H, ranging from 0.5 to 5.5, preferably from 1.5 to 5.0, more preferably from 2.0 to 4.5. In a particular embodiment, the ranges of the carbon to hydrogen weight ratio, mentioned herein, may be observed when the alcohol was contacted with the modified crystalline aluminosilicate at atmospheric pressure, at temperatures between 100 and 500° C., and with an alcohol weight hour space velocity from 1.3 to 3.1 $h^{-1}$. A low C/H ratio at the end of the catalytic process allows a fast and convenient regeneration of the catalyst composition. In particular, when the catalyst composition consists of the modified crystalline aluminosilicate as defined above, the carbon to hydrogen weight ratio C/H as defined herein refers to the carbon to hydrogen weight ratio C/H on the modified crystalline aluminosilicate after having been used in the process according to the present invention, i.e. on the spent modified crystalline aluminosilicate.

In a preferred embodiment, at least 80% wt of the olefins recovered in step (d) have the same number of carbon atoms as the alcohol provided in step (a), preferably at least 85% wt, more preferably at least 90% wt, in particular at least 95% wt.

In a preferred embodiment, the present process is carried out with a mixture of butanol as alcohol, preferably isobutanol, and the mixture of olefins produced comprises at least 80% wt of butene and isomers thereof, preferably at least 90%, more preferably at least 95% wt, most preferably at least 98% wt. In addition, the selectivity in n-butenes may be at least 65% wt based on the total amount of butene and isomers thereof contained in the mixture of olefins produced, preferably at least 70% wt.

In another preferred embodiment, the process according to the present invention is carried out with ethanol as alcohol and ethylene is produced. The reaction yield may be at least 80% wt, preferably at least 95% wt.

In another preferred embodiment, the process according to the present invention is carried out with a mixture of propanol as alcohol and propylene is produced. The reaction yield may be at least 80% wt, preferably at least 90% wt.

In another preferred embodiment, the process according to the present invention is carried out with a mixture of hexanol, i.e. alcohol having 6 carbon atoms as defined above, and the mixture of olefins produced comprises at least 80% of hexene and isomers thereof.

In another aspect of the present invention, the mixture of olefins produced according to the present process may be used as starting material for subsequent reactions such as the production of propylene via metathesis process, the production of butadiene via dehydrogenation, oligomerization, as well as for the production of transportation fuels, monomers and fuel additives. The mixture of olefins produced according to the present process may also replace the use of raffinate I in the refinery or petrochemical plants. The most typical application of a mixture containing isobutene is the conversion of the said isobutene into ethers (MTBE and ETBE), into t-butylalcohol (TBA) or oligomers (e.g. di/tri-iso-butenes), all being gasoline components. The higher oligomers of isobutene can be used for jet fuel applications.

High purity isobutene can further be made by the decomposition of ethers (backcracking) or TBA (dehydration). High purity isobutene finds applications in the production of butyl-rubber, poly-isobutene, methylmethacrylate, isoprene, hydrocarbons resins, t-butyl-amine, alkyl-phenols and t-butyl-mercaptan. When the mixture of olefins contains n-butenes which have not reacted during the production of ethers or TBA and substantially not or only to a limited extend during the oligomerisation, said n-butenes have applications in the production of sec-butanol, alkylate (addition of isobutane to butenes), polygasoline, oxo-alcohols and propylene (metathesis with ethylene or self-metathesis between but-1-ene and but-2-ene). By means of super fractionation or extractive distillation or absorptive separation but-1-ene can be isolated from the n-butenes mixture. But-1-ene is used as comonomer for the production of polyethylenes, for polybut-1-ene and n-butyl-mercaptan. n-Butenes can also be separated from isobutene by means of a catalytic distillation. This involves an isomerisation catalyst that is located in the distillation column and continuously converts the but-1-ene into but-2-ene, being a heavier component than but-1-ene. Doing so, a bottom product rich in but-2-ene and a top product poor in but-1-ene and rich in isobutene is produced. The bottom product can be used as described above. One main application of such but-2-ene rich stream is the metathesis with ethylene in order to produce propylene. If high purity iso-butene is desired the top product can be further super fractionated into substantially pure iso-butene and pure but-1-ene or the isobutene can be isolated via formation of ethers or TBA that is subsequently decomposed into pure iso-butene. The n-butenes rich stream may be used for the production of butadiene via dehydrogenation or oxidative dehydrogenation or send to alkylation unit to produce bio-alkylate. The mixture of isobutene and butenes can be sent to a catalytic cracking which is selective towards light olefins in the effluent, the process comprising contacting said isobutene and butenes mixture with an appropriate catalyst to produce an effluent with an olefin content of lower molecular weight than that of the feedstock. Said cracking catalyst can be a silicalite (MFI or MEL type) or a P-ZSM5.

In another aspect of the present invention, the catalyst composition according to the present invention, and preferably prepared according to the present invention, is suitable for the production of a mixture of olefins having at least two carbon atoms from alcohols having at least two carbon atoms. Preferably, at least 80% of the olefins produced have the same number of carbon atoms as the alcohol. Preferably, the alcohol is isobutanol and the olefins comprise at least 95% of butene and isomers thereof.

EXAMPLES

Procedure to Determine the Si/Al Framework Molar Ratio

The ratio is determined using solid-state $^{29}$Si NMR. All solid state $^{29}$Si MAS NMR spectra were recorded on a Bruker DRX500 spectrometer (Pulse 45°, Relaxation delay 7 sec, rotor 4 mm). For a low defect zeolite samples, an aluminium atom will always be surrounded by four Silicones. The $^{29}$Si NMR spectra of aluminosilicate zeolites give typically a series of peak which correspond to $SiO_4$ tetrahedra in five different possible environments corresponding to different number of $AlO_4$ tetrahedra connected to the silicon via oxygen. For simplicity, these sites will be denoted ignoring the oxygen atoms as Si (4-nAl), where n is a number of Si in the tetrahedral:Si(0Al), Si(1Al), Si(2Al), Si(3Al), Si(4Al). The intensity of a silicon resonance is proportional to the number of associated silicon atoms. The number of Al atoms is proportional to a sum of the each corresponding peak multiplied by a number of Al (4-n) and divide by 4. The intensity of each resonance is determined by deconvolution: Si(0Al), Si(1Al), Si(2Al), Si(3Al), Si(4Al).

The Si/Al ratio is then given by the following equation:

Si/Al=4*Si total area/[Area Si(1Al)+2*Area Si(2Al)+3*Area Si(3Al)+4*Area Si(4Al)]

Procedure to Determine the Ratio of Strong Acid Sites to Weak Acid Sites S/W

The measurement of Temperature-programmed desorption of ammonia is performed in a Pyrex®™ cell containing about 0.4 g of sample in form of the fraction 35-45 mesh. The cell is placed in an oven of the AUTOCHEM II 2920 equipped with TCD detector and the following steps are carried out:

Activation: this step is performed under a flow rate of dried (over molecular sieve e.g. 3 A or 4 A) He of 50 cm$^3$/min (<0.001% of water). The temperature is increased from room temperature to 600° C. with a rate of 10° C./min. The temperature is then maintained at 600° C. during 1 h. The temperature is then decreased to 100° C. with a rate of 10° C./min.

Saturation: this step is performed at 100° C. During a first hour, the solid is put in contact with a flow of 30 cm$^3$/min of a dried (over molecular sieve e.g. 3 A or 4 A, <0.001% of water) mixture of 10 weight % of $NH_3$ diluted in He. Then, during the next 2 h, the solid is put in contact with a flow rate of 50 cm$^3$/min of dried (over molecular sieve e.g. 3 A or 4 A, <0.001% of water) He to remove the physisorbed $NH_3$.

Analysis: this step is performed under a flow of 50 cm$^3$/min of dried (over molecular sieve e.g. 3A or 4A, <0.001% of water) He. The temperature is increased to 600° C. with a rate of 10° C./min. Once the temperature of 600° C. has been reached, it is maintained for 1 h. The cell is then cooled down and weighted. The amount of $NH_3$ desorbed from the solid is referenced to the weight of the sample.

Calculation: The area of the ammonia desorbed above 340° C. is defined as amount of the "strong" acid sites (S). The amount of the "weak" acid sites (W) is defined as a difference between the total area and the amount of the ammonia desorbed above 340° C.

Procedure to Determine the EFAL Content via $^{27}$Al NMR

The EFAL content was measured via $^{27}$Al NMR. The $^{27}$Al MAS NMR is performed on hydrated samples over a night in presence of saturated aqueous solution of KCl. NMR spectra were measured with the help of a MAS 4 mm probe on a Bruker DRX (500 MHz) spectrometer. Rotation speed of the sample was of 15000 Hz. The EFAL content is then calculated with the ratio of the area of the peak of Al(VI) at 0 ppm+Al(V) at 35 ppm relative to total area of the peak of the spectrum obtained by deconvolution (i.e. the area of the peak of Al(VI) at 0 ppm+Al(V) at 35 ppm+Al(IV) at 55 ppm).

Procedure to Determine the Weight Ratio Between C and H in Spent Catalyst Composition The spent (after reaction) catalyst is purged with an inert gas for 2 h in the reactor at 300° C. (10 Nl/h $N_2$, He, etc.) to desorb the physisorbed hydrocarbons. Then the carbon and hydrogen content is analyzed by CHN (ethylene diaminetetraacetic acid (EDTA) standard, calibration curve for the range 0.5-10% of carbon). The analysis is performed according the following operating conditions:

Catalyst weight: 200 mg
Combustion Temperature: 950° C.
Catalyst Heater Temperature: 700° C.
IR Oven Temp: 50° C.
He Flow Controller temp: 40° C.
TC Filament Current: 8.90 volts
Ballast Pressure (mm Hg): P atm.
Carbon IR Cell: 1.75 volts
Hydrogen IR Cell: 1.41 volts
Nitrogen TC Cell: 8.77 volts
The value of hydrogen is corrected to humidity value, which is measured by ThermoGravimetric Analysis (TGA) loss at 200° C. (10° C./min, He-flow) with a for 30 min in He at 200° C. We assume that the 100% of loss corresponds to the water content because the sample has been already treated at 300° C. to remove the physisorbed hydrocarbons.

General Procedure for Dehydration Process of Alcohols

A stainless-steel reactor tube having an internal diameter of 10 mm is used. 10 ml of the catalyst composition, as pellets of 35-45 mesh, is loaded in the tubular reactor. The void spaces, before and after the catalyst composition, are filled with SiC granulates of 2 mm. The temperature profile is monitored with the aid of a thermocouple well placed inside the reactor at the top of catalyst bed. Before the reaction, the catalyst was pretreated in nitrogen flow at 550° C. for 2 h (heating rate 60° C./h) followed by cooling down to the reaction temperature. The nitrogen is then replaced by the feed at the indicated operating conditions. The catalytic tests are performed down-flow, in a pressure range from 0.5 to 10 barg, in a temperature range of 100-500° C. and with an alcohol weight hour space velocity varying from 0.1-20 $h^{-1}$ (kg of product/hours×kg of catalyst). Analysis of the products is performed by using an on-line gas chromatography.

Example 1

10 g of a sample of calcined powder FER55 (CP914 from Zeolyst international) having a Si/Al of 32 and S/W of 1.0 was treated with an aqueous solution of citric acid having a concentration of 0.1M at room temperature. Then, the solution was put in an ultrasonic bath for 30 min or stirred for 30 min in a beaker, filtrated and washed with 5 L of deionized water, dried at 120° C. overnight and calcined at 550° C., 1° C./min in flow of air (10 NI/h) for 6 h to form a modified crystalline aluminosilicate of FER structure according to the present invention having S/W ratio of 0.95. Isobutanol has been reacted on the catalyst at atmospheric pressure, at temperatures between 100 and 500° C., and with an isobutanol weight hour space velocity (WHSV) from 1.3 to 3.1 $h^{-1}$. In these operating conditions, starting from 200° C., isobutanol conversion was complete with selectivity to butenes of 99.2%. The ratio of 2-butenes to butenes was 0.75. The results presented in table 1 were obtained with a temperature of 200° C., WHSV of 3.1 $h^{-1}$ at atmospheric pressure.

Example 2

10 g of a sample of calcined powder FER55 structure (CP914 from Zeolyst international) having a Si/Al of 32 and S/W of 1.0 was suspended in 200-250 mL of 0.05M aqueous solution of disodium ethylene diamine tetracetic acid salt at room temperature. The suspension was heated at 75° C. for 16 h, filtrated and washed with 10 L of deionized water. The sample was further treated two times with 200 mL of 0.2M of $NH_4NO_3$ solution at room temperature for 4 h and washed with at least 2 L of deionized water each time, dried at 120° C. overnight and calcined at 550° C. for 6 h (1° C./min, in flow of air, 10 NI/h) to form a modified crystalline aluminosilicate of FER structure according to the present invention having a S/W ratio of 0.64. The content of sodium in the modified crystalline aluminosilicate is of 1% wt. Isobutanol has been reacted on the catalyst at atmospheric pressure, at temperatures between 100 and 500° C., and with an isobutanol weight hour space velocity (WHSV) from 1.3 to 3.1 $h^{-1}$. In these operating conditions, starting from 200° C., isobutanol conversion was complete with selectivity to butenes of 98.9%. The ratio of 2-butenes to butene was 0.73. The results presented in table 1 were obtained with a temperature of 200° C., WHSV of 3.1 $h^{-1}$ at atmospheric pressure.

Example 3

10 g of a sample of calcined powder FER55 structure (CP914 from Zeolyst international) having a Si/Al of 32 and S/W of 1.0 was used as comparative catalyst. Isobutanol has been reacted on the catalyst at atmospheric pressure, at temperatures between 100 and 500° C., and with an isobutanol weight hour space velocity (WHSV) from 1.3 to 3.1 $h^{-1}$. In these operating conditions, starting from 200° C., isobutanol conversion was complete with selectivity to butenes of 98.9%. The ratio of 2-butenes to butene was 0.74. The results presented in table 1 were obtained with a temperature of 200° C., WHSV of 3.1 $h^{-1}$ at atmospheric pressure.

Example 4(Comparative)

10 g of a sample of calcined powder FER55 structure having a Si/Al of 32 and S/W of 1.0 was subjected to a treatment at 600° C. for 6 h in 100% of steam. The treatment led to the S/W–0.5 but created a lot of extra framework Al (EFAL 37.2%). The sample was used as comparative catalyst. Isobutanol has been reacted on the catalyst at atmospheric pressure, at temperatures 200° C., and with an isobutanol weight hour space velocity (WHSV) 3.1 h–1. In these operating conditions, isobutanol conversion was only 90.8% with selectivity to butenes of 98.9%. The ratio of 2-butenes to butenes was 0.70.

Table 1 hereunder shows results obtained with catalysts of examples 1-4.

TABLE 1

Properties of catalysts of the invention and of comparative catalysts, and results obtained therewith in a process for dehydration of isobutanol

| Examples | Ratio S/W | C4= selectivity | 2-butene/ butenes | C, wt % | Ratio C/H | % EFAL* ($^{27}$Al MAS NMR) |
|---|---|---|---|---|---|---|
| Example 1 (invention) 10/8051 | 0.95 | 99.2% | 0.75 | 3.51 | 3.9 | 1.7 |
| Example 2 (invention) 10/8371 | 0.64 | 98.9% | 0.73 | 2.12 | 2.8 | 6.0 |
| Example 3 (comparative) 81/1560 | 1.0 | 98.9% | 0.74 | 3.67 | 5.7 | 1.3 |
| Example 4 (comparative) 82/5084 | 0.50 | 92.9 | 0.70 | 1.26 | 3.9 | 37.2 |

TABLE 1-continued

Properties of catalysts of the invention and of
comparative catalysts, and results obtained therewith
in a process for dehydration of isobutanol

| Examples | Ratio S/W | C4= selec- tivity | 2-butene/ butenes | C, wt % | Ratio C/H | % EFAL* ($^{27}$Al MAS NMR) |
|---|---|---|---|---|---|---|

*area of Al(VI) + Al(V) relative to total area of the spectrum obtained by deconvolution The catalysts according to the present invention have excellent $C_4$ selectivity and especially 2-butene selectivity in the reaction of dehydration of isobutanol. The catalysts according to the present invention, after being used in the dehydration process of alcohol, have less coke or aromatics residues on their external surface which results in lower C weight. Furthermore, in the spent catalyst composition, the coke is softer, represented by a lower C/H ratio compared to the comparative catalyst. A lower C/H weight ratio allows the improvement of the regenerability of said catalyst composition. In addition, when lower residues are formed on the external surface of the catalyst, the loss of catalyst activity through deactivation is strongly reduced. Another effect of a low C/H weight ratio is a weak deactivation of the catalyst over time resulting in better productivity thereof.

As shown by the present example, the catalysts according to the present invention has several advantages compared to the catalysts known in the art. Furthermore, the catalysts according to the present invention are suitable for a wide range of alcohols.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

In another embodiment 1, the invention relates to a catalyst composition comprising a modified crystalline aluminosilicate of the Framework Type FER having Si/Al framework molar ratio greater than 20 characterized in that in said modified crystalline aluminosilicate the ratio between the strong acid sites and the weak acid sites, S/W, is lower than 1.0; the ratio S/W being measured by temperature-programmed desorption of ammonia and being determined by the ratio of the peak area of ammonia desorbed above 340° C. to that desorbed below 340° C.

In an embodiment 2, the invention relates to a catalyst composition according to the previous embodiment wherein said modified crystalline aluminosilicate is ferrierite.

In an embodiment 3, the invention relates to a catalyst composition according to any of the previous embodiments wherein said modified crystalline aluminosilicate of the Framework Type FER has Si/Al framework molar ratio ranging from 20 to 150, preferably ranging from 21 to 100, more preferably ranging from 25 to 50.

In an embodiment 4, the invention relates to a catalyst composition according to any of the previous embodiments wherein said modified crystalline aluminosilicate of the Framework Type FER has a ratio between the strong acid sites and the weak acid sites, S/W, lower than 0.96.

In an embodiment 5, the invention relates to a catalyst composition according to any of the previous embodiments wherein said modified crystalline aluminosilicate has content in metals or cations thereof lower than 1000 ppm, said metals belonging to columns 3 to 12 of the Periodic Table.

In an embodiment 6, the invention relates to a catalyst composition according to any of the previous embodiments wherein said modified crystalline aluminosilicate comprises the sequences —[—Al—O(H)—Si—]— and —[—Al—O(X)—Si—]— wherein X is alkali ions, alkaline earth ions or silver ions, the sequence —[—Al—O(X)—Si—]— representing less than 75% based on the total amount of sequences —[—Al—O(H)—Si—]— and —[—Al—O(X)—Si—]— in said modified crystalline aluminosilicate, preferably less than 50%, more preferably less than 25%, and preferably at least 1%, more preferably at least 5%, most preferably at least 10%.

In an embodiment 7, the invention relates to a process for the preparation of a catalyst composition according to any of the previous embodiments comprising the steps of:
  (A) providing a crystalline aluminosilicate of the Framework Type FER having Si/Al framework molar ratio greater than 20, and
  (B) treating said crystalline aluminosilicate to form a modified crystalline aluminosilicate of the Framework Type FER wherein the Si/Al framework molar ratio is greater than 20, and wherein the ratio of strong acid sites to weak acid sites S/W is lower than 1.0.

In an embodiment 8, the invention relates to a process according to the previous embodiment wherein said treatment of step (B) to form said modified crystalline aluminosilicate of the Framework Type FER comprises one or more of the following steps:
  (i) treating said the crystalline aluminosilicate of the Framework Type FER with an acidic medium, preferably contacting said crystalline aluminosilicate of the Framework Type FER with a solution containing one or more organic medium, each medium comprising one or more —CO$_2$H, —SO$_3$H or —SO$_4$H groups or salts thereof;
  (ii) applying partial ion exchange to the crystalline aluminosilicate of the Framework Type FER, preferably contacting said crystalline aluminosilicate of the Framework Type FER with a solution containing one or more salts of nitric acid, halogenic acid, sulfuric acid, sulfurous acid or nitrous acid or mixture thereof, said salt being ammonium, calcium, lithium, sodium, potassium, magnesium or silver;
  (iii) selectively poisoning strong acid sites of the crystalline aluminosilicate of the Framework Type FER by adding a solution comprising alkali salts or alkaline earth salts.

In an embodiment 9, the invention relates to a dehydration process of alcohols for the production of a mixture of olefins comprising the steps of:
  (a) providing an alcohol having at least two carbon atoms, and preferably at most 7 carbon atoms, or mixture thereof with the proviso that the alcohols contained in the mixture have the same number of carbon atoms, and
  (b) introducing in a reactor a stream (S1) comprising said alcohol, and optionally water and optionally an inert component,
  (c) contacting said stream (S1) with a catalyst composition according to any of the previous embodiments 1 to 6, preferably prepared according to embodiments 7 or 8, under conditions suitable for producing a mixture of olefins having the same number of carbon atoms as the alcohol, (d) recovering from said reactor a stream (S2), optionally removing water and the inert component and if any unconverted alcohol to get a mixture of olefins having the same number of carbon atoms as the alcohol.

In an embodiment 10, the invention relates to a process according to the previous embodiment wherein the WHSV of the alcohol ranges from 0.1 h$^{-1}$ to 20 h$^{-1}$, preferably from 0.5 h$^{-1}$ to 10 h$^{-1}$, more preferably from 0.1 h$^{-1}$ to 9 h$^{-1}$.

In an embodiment 11, the invention relates to a process according to any of the previous embodiments 9 or 10 wherein step (c) is carried out at reaction temperature ranging from 200° C. to 500° C., advantageously from 220° C. to 500° C. and preferably from 230° C. to 450° C.

In an embodiment 12, the invention relates to a process according to any of the previous embodiment 9 to 11 wherein step (c) is carried out at pressure ranging from 0.5 to 30 bars absolute, advantageously from 0.5 to 10 bars absolute, advantageously from 0.5 to 9 bars absolute.

In an embodiment 13, the invention relates to the process according to any of the previous embodiments 9 to 12, wherein the alcohol is provided from biomass fermentation or biomass gasification to syngas followed by a modified Fischer-Tropsch synthesis.

In an embodiment 14, the invention relates to the use of a mixture of olefins produced by the process according to any of the previous embodiments 10 to 13 in production of propylene via metathesis process, production of butadiene via dehydrogenation, oligomerization, as well as for the production of transportation fuels, monomers and fuel additives.

In an embodiment 15, the invention relates to the use of a catalyst composition according to any of the previous embodiments 1 to 6 for the production of a mixture of olefins from alcohols, the latter being isobutanol or a mixture of butanol, and the mixture of olefins produced contains at least 80% of butenes and the selectivity in n-butenes is at least 65% based on the total amount of butenes and isomers thereof contained in the mixture of olefins.

The invention claimed is:

1. A catalyst composition, for the dehydration of alcohols to olefins having the same number of carbons, comprising a modified crystalline aluminosilicate wherein said modified crystalline aluminosilicate is of the Framework Type FER having Si/Al framework molar ratio greater than 20;

wherein said modified crystalline aluminosilicate comprises an extra framework aluminum, (EFAL) content lower than 15 wt % as measured by $^{27}$Al MAS NMR;

wherein said modified crystalline aluminosilicate comprises a ratio between the strong acid sites and the weak acid sites, S/W which is lower than 1.0; the ratio S/W being measured by temperature-programmed desorption of ammonia and being determined by the ratio of the peak area of ammonia desorbed above 340° C. to that desorbed below 340° C.; and said modified crystalline aluminosilicate is prepared from a crystalline aluminosilicate which is not steamed and is prepared with either one or both of the following treatments:

said crystalline aluminosilicate is treated with an organic acidic medium, an organic medium, or combinations thereof;

strong acid sites of said crystalline aluminosilicate are selectively poisoned with alkali salts or alkaline earth salts or silver so that the weight percent of alkali or alkaline earth or silver on the catalyst composition is of at least 0.5% weight, as measured by chemical analysis with the method ASTM UOP961-12.

2. A catalyst composition according to claim 1 wherein said modified crystalline aluminosilicate is ferrierite.

3. A catalyst composition according to claim 1 wherein said modified crystalline aluminosilicate is prepared without being calcined or with a calcination in a calcination reactor at a temperature not higher than 600° C. and with a temperature increase of less than 10° C./min, for a period of at least 30 min and under a gas flow containing at most 1000 ppm volume of water measured at the inlet of the calcination reactor.

4. A catalyst composition according to claim 1 wherein said acidic medium or said organic medium is selected from the group consisting of citric acid, tartaric acid, maleic acid, ethylene di-amine tetracetic acid (EDTA), or their corresponding salts.

5. A catalyst composition according to claim 1 wherein said modified crystalline aluminosilicate of the Framework Type FER has Si/Al framework molar ratio ranging from 20 to 150.

6. A catalyst composition according to claim 1 wherein said modified crystalline aluminosilicate of the Framework Type FER has a ratio between the strong acid sites and the weak acid sites, S/W, lower than 0.96.

7. A catalyst composition according to claim 1 wherein said modified crystalline aluminosilicate has a content in metals or cations thereof lower than 1000 wt ppm measured with the method ASTM UOP961-12, said metals belonging to columns 3 to 12 of the Periodic Table excluding silver.

8. A catalyst composition according to claim 1 wherein said modified crystalline aluminosilicate comprises the sequences —[—Al—O(H)—Si—]— and —[—Al—O(X)—Si—]— wherein X is alkali ions, alkaline earth ions or silver ions, the sequence —[—Al—O(X)—Si—]— representing less than 75% wt based on the total amount of sequences —[—Al—O(H)—Si—]— and —[—Al—O(X)—Si—]— in said modified crystalline aluminosilicate as measured via solid-state $^{29}$Si NMR.

* * * * *